(12) United States Patent
Ballsieper (10) Patent No.: US 9,538,965 B2
(45) Date of Patent: Jan. 10, 2017

(54) MOVABLE RADIATION PROTECTION ARRANGEMENT

(71) Applicant: MAVIG GMBH, Munich (DE)

(72) Inventor: Barbara Ballsieper, Munich (DE)

(73) Assignee: MAVIG GMBH, Munich (DE)

( * ) Notice: Subject to any disclaimer, the term of this patent is extended or adjusted under 35 U.S.C. 154(b) by 0 days.

(21) Appl. No.: 14/772,627

(22) PCT Filed: Mar. 5, 2014

(86) PCT No.: PCT/EP2014/054249
§ 371 (c)(1),
(2) Date: Sep. 3, 2015

(87) PCT Pub. No.: WO2014/135582
PCT Pub. Date: Sep. 12, 2014

(65) Prior Publication Data
US 2016/0015336 A1  Jan. 21, 2016

(30) Foreign Application Priority Data

Mar. 6, 2013 (DE) .......................... 10 2013 203 812

(51) Int. Cl.
*G21F 3/00* (2006.01)
*A61B 6/10* (2006.01)

(52) U.S. Cl.
CPC ................ *A61B 6/107* (2013.01); *G21F 3/00* (2013.01)

(58) Field of Classification Search
USPC ......... 250/505.1, 515.1, 516.1, 517.1, 518.1, 250/519.1
See application file for complete search history.

(56) References Cited

U.S. PATENT DOCUMENTS 3,308,297 A   3/1967   Mansker
4,460,833 A * 7/1984  Malamud ............... A61B 6/107
                                                              250/515.1
(Continued)

FOREIGN PATENT DOCUMENTS

DE          20307606 U1    10/2003
DE       102004001328 A1    4/2005
(Continued)

OTHER PUBLICATIONS

International Search Report dated Jun. 11, 2014 issued in PCT/EP2014/054249.
(Continued)

*Primary Examiner* — Nicole Ippolito
(74) *Attorney, Agent, or Firm* — Scully Scott Murphy and Presser; Frank DiGiglio (57) ABSTRACT

The invention relates to a movable radiation protection system comprising
a frame which is open on one side and comprises a lower part and an upper part, said upper part being vertically adjustable relative to the lower part,
at least two flexible radiation protection drapes for protecting against radiation, preferably X-ray radiation,
wherein a first of the at least two radiation protection drapes is attached to the lower part of the frame and preferably extends to the lower edge of the frame, and
wherein a second of the at least two radiation protection drapes is attached to the upper part of the frame and is formed such that the at least two radiation protection drapes overlap in each vertical position in which the upper part is adjusted relative to the lower part.

21 Claims, 8 Drawing Sheets

(56) References Cited

U.S. PATENT DOCUMENTS

| | | | | |
|---|---|---|---|---|
| 5,015,864 A * | 5/1991 | Maleki | ............... | G21F 3/02 |
| | | | | 250/515.1 |
| 7,829,873 B2 * | 11/2010 | Fox | ............... | A61B 6/107 |
| | | | | 250/505.1 |
| 2006/0049384 A1 | 3/2006 | Eder | | |
| 2009/0272921 A1 | 11/2009 | Ballsieper | | |
| 2012/0228439 A1 | 9/2012 | Hassid | | |
| 2013/0270462 A1 * | 10/2013 | Beck | ............... | A61B 6/4423 |
| | | | | 250/516.1 |

FOREIGN PATENT DOCUMENTS

| | | |
|---|---|---|
| DE | 102006028958 A1 | 12/2007 |
| DE | 102009037565 A1 | 2/2011 |
| EP | 0345548 A1 | 12/1989 |
| WO | WO 2012/116030 A1 | 8/2012 |

OTHER PUBLICATIONS

English Abstract of WO 2011/018459 A1, dated Feb. 17, 2011.
English Abstract of EP 1477992 A1, dated Nov. 17, 2004.

* cited by examiner

Figure 7b

MOVABLE RADIATION PROTECTION ARRANGEMENT

The present invention relates to a movable radiation protection system comprising one or more flexible radiation protection drapes. This movable radiation protection system is especially suitable for use in interventional radiology and corresponding surgical interventions. The movable radiation protection system serves for protecting staff members, such as the physician or assistants, against radiation, in particular X-ray radiation.

DE 203 07 606 U1 discloses a movable radiation protection system having a transparent radiation protection shield which is curved and fixed to a double cross-shaped base. The arms of the base have different lengths so as to reduce the risk of tilting of the radiation protection device. The radiation protection device is provided with a height adjustment means and comprises symmetrical or asymmetrical recesses in the radiation protection shield, which are provided to allow reaching through the radiation protection shield and thus a larger operating range and more free moving space.

EP 0 345 548 A1 relates to a radiation shielding device having a radiation shielding wall that absorbs X-rays, the radiation shielding wall being mounted on a supporting, freely movable carriage. The radiation shielding device further comprises a height-adjustable holder for two wall members, the first wall member being disposed below the second, transparent wall member and the second wall member being capable of swivelling around a horizontal axis.

U.S. Pat. No. 5,015,864 discloses a mobile radiation shielding device, wherein a radiation protection suit is attached to a mobile frame.

U.S. Pat. No. 3,308,297 relates to a movable radiation protection shield, which has in its centre an aperture with a guided tray, so that the attending personnel may reach through this tray through the radiation protection shield.

It is the object of the present invention to provide a movable radiation protection system which can be moved easily and effortlessly by the medical personnel during an interventional treatment.

This object is achieved with a movable radiation protection system according to the patent claims.

The movable radiation protection system of the present invention is in particular suitable for being easily moved by a single person.

The basic idea underlying the present invention is to attach a plurality of flexible radiation protection drapes to a two-part movable frame in such a way that the two-part frame is vertically adjustable and the radiation protection drapes overlap in each vertical position, so that the medical personnel enjoys optimum radiation protection. Moreover, using flexible radiation protection drapes, in contrast to rigid radiation protection shields, significantly reduces the weight of the present radiation protection system. At the same time, such a movable radiation protection system can at all times be easily controlled by the user, close to the body, both in a standing or sitting posture. The overlapping of the flexible radiation protection drapes ensures that the operator is always shielded from radiation at any vertical position of the movable radiation protection system.

The invention has the advantage that one of the flexible radiation protection drapes preferably reaches to the lower edge of the radiation protection system. Therefore, no radiation can reach the operator to be protected even in this area. At the same time, however, the use of a flexible radiation protection drape enables the safe actuation of foot petals of the medical instruments to be used. For this reason, the chassis of the movable radiation protection system is designed such that the foot of the operator can reach the foot petals of the medical instruments with ease, i.e. that a passage is formed over the entire height of the chassis. Through this passage, the operator's foot can reach the foot pedal unimpeded. However, in view of its flexibility, the protective drape need not be opened for this purpose rather it can be pushed forward before the foot or leg. As a result, the foot or leg is optimally protected against radiation during actuation of the foot petal.

The invention relates to a movable radiation protection system comprising a frame which is open on one side and which comprises a lower part and an upper part, the upper part being vertically adjustable relative to the lower part, at least two flexible radiation protection drapes for protection against radiation, preferably X-ray radiation. A first of the at least two radiation protection drapes is attached to the lower part of the frame and extends to the lower edge of the frame. Furthermore, a second of the at least two radiation protection drapes is attached to the upper part of the frame and designed such that the at least two radiation protection drapes overlap in each vertical position in which the upper part is set relative to the lower part.

In a further embodiment, the lower frame further comprises a chassis which may comprise a plurality of steering rollers, such as four steering rollers.

According to a further embodiment, the chassis is designed such that a passage is provided over the entire height of the chassis at the side opposite to the open side of the frame.

In a further embodiment, the chassis comprises a first and a second, preferably arcuate cantilever arm to which the steering rollers are attached. The arcuate cantilever arm may have the form of a foot. The chassis has ground contact with the floor not directly with the foot but with the steering rollers attached to the foot.

In a further embodiment, the lower frame may comprise a first and a second side part. Here, the first cantilever arm of the chassis can be attached to the first side part and the second cantilever arm of the chassis can be attached to the second side part.

According to a further embodiment, the first and the second side parts comprise first and second tubes in the vertical direction. The first and second tubes of the first side part are connectable with each other by cross connections and the first and second tubes of the second side part are likewise connectable with each other by cross connections.

In a further embodiment, covers are attached between the first and second tubes of the respective first and second side parts.

According to a further embodiment, the first and the second side part can be connected by a crossbar. According to this embodiment, the cross connection is provided at the side of a frame opposite to the open side of the frame.

According to a further embodiment, the lower part preferably comprises a bow-shaped connecting element which is attached to the first and second tubes. The preferably bow-shaped connecting element can be attached to the upper edges of the first and second tubes in such a way that it forms the top end thereof. According to the invention, on the inside and the outside of the preferably bow-shaped connecting element shank buttons may be provided, on which one or more radiation protection drapes are mounted. Thus, it is possible to mount flexible radiation protection drapes on the inside of the frame and/or on the outside of the frame depending on the radiation dose. A radiation protection drape is in particular flexible when it is designed such that in view of its structure it adapts to the outward shape of the frame and/or when it can be brought into another form by simple manual manipulation. A flexible radiation protection drape can in particular be readily bendable, yielding, adjustable and/or elastic.

In accordance with the invention, the connecting element can be in the form of a semicircle, of a half rectangle with rounded edges or of a half polygon. However, the form of the connecting element is not restricted to these forms. Thus, for example, a three-quarter circle or a full circle is also possible. Especially in the case of a three-quarter circle or of a full circle it is of advantage to segment the connecting element by one or more movable and lockable hinges. By folding up the segmented connecting element, it becomes easier for the user of the movable radiation protection system to enter the radiation protection system.

In a further embodiment, the upper part has a plurality of supporting rods and the lower part has a plurality of bearing bushes. The supporting rods of the upper part can be moved to and fro in a corresponding bearing bush each for adjusting the vertical position. Moreover, the upper part may comprise a preferably arcuate connecting element. In this case, the arcuate connecting element of the upper part is not restricted to a specific form either, but may likewise have the form of a semicircle, of a three-quarter circle or of a full circle, of a half rectangle with rounded edges, or of a half polygon. In case of an above-described segmentation of the connecting element of the lower part it is further advantageous when the connecting element of the upper part likewise shows a corresponding segmentation.

According to a further embodiment, a part of the bearing bushes is fitted in the connecting element of the lower part and the other part of the bearing bushes is fitted in the first and second tubes of the lower part.

In a further embodiment, the arcuate connecting element of the upper part is mounted on the supporting rods. The preferably arcuate connecting element of the upper part can be attached to the upper end of the supporting rods in such a way that it ends flush therewith.

In a further embodiment, the movable radiation protection system comprises a counterweight or a counter-acting spring suitable for compensating the weight of the upper part and of the radiation protection drape(s) mounted on the upper part, which is/are mounted on the upper part of the frame. Here, the counterweight or the counter-acting spring is provided on the lower part of the chassis and connected to the upper part of the chassis, for example by a cable pull/cable pull system. Ideally, the counterweight or the counter-acting spring balances the weight of the upper part and of the radiation protection drape(s) mounted on the upper part in such a way that, without further fixation, the upper part and the radiation protection drapes mounted thereon remain in their position without further aids.

According to a further embodiment, the lower part comprises a retaining device suitable for retaining at least one of the plurality of supporting rods of the upper part such that the upper part is locked in a position in which it is inserted into the lower part. According to the invention, such a retaining device is used in particular when no counterweight or counter-acting spring is present, or when there is insufficient taring of the counterweight or the counter-acting spring.

In a further embodiment, the flexible radiation protection drapes comprise at least one material containing an element with an atomic number of from 50 to 83. Such an element may inter alia be tin, wolfram, gadolinium, antimony, bismuth, lead or barium.

In a further embodiment, a radiation protection drape can have a lead substitute material as light-weight radiation protection material for application in a large energy range, as described, for example in DE 10 2004 001 328 A1. Furthermore, the radiation protection drape may comprise a laminated lead-free X-ray shielding material from individual composite layers, as disclosed in DE 10 2006 028 958 A1. The radiation protection drape may also comprise a coated microfibrous web according to DE 10 2009 037 565 A1.

In the following, the invention will be explained in more detail on the basis of examples and the Figures.

Figure 1:
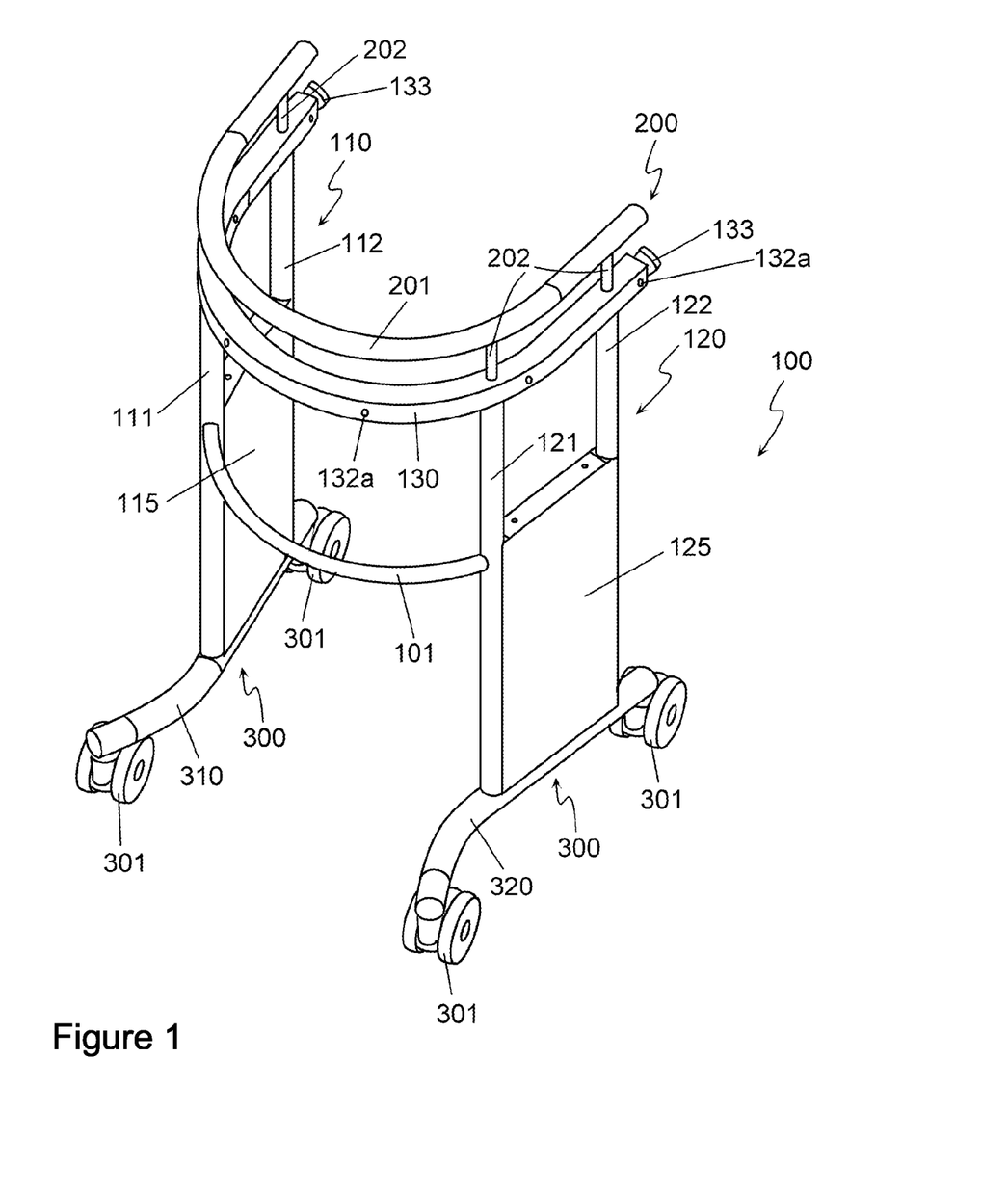
FIG. 1 shows a perspective view of a movable radiation protection system without radiation protection drapes according to a first preferred embodiment of the present invention.

FIG. 1 shows a perspective view of a movable radiation protection system according to a first embodiment of the present invention. For reasons of simplicity, the radiation protection drapes are not shown. The frame of the movable radiation protection system has a lower part 100. The lower part 100 in turn has a first side part 110 and a second side part 120. A first tube 111, 121 and a second tube 112, 122 form the base frame of the first side part 110 and of the second side part 120, respectively, with the first and second tubes 111, 121, 112, 122 extending in vertical direction, and the first tubes 111, 112 being connected to the second tubes 112, 122 by first cross connections 113, 123 and second cross connections 114, 124 (see FIG. 2). The first side part 110 and the second side part 120 are connected to each other by a crossbar 101 approximately at a half to two thirds of the height of the side parts. The crossbar is attached to the respective first tubes 111, 121 of the first side part 110 and the second side part 120. Thus, an open side is formed between the second tubes 112, 122. The crossbar 101 is mounted at such a height that it does not impede a foot or leg of the operator, which is conveniently extended forwardly in the direction of escape to reach a foot petal.

Cover panels 115, 125 covering the space between the first tubes 111, 121 and the second tubes 112, 122 are provided between the first tubes 111, 121 and the second tubes 112, 122.

Figure 2:
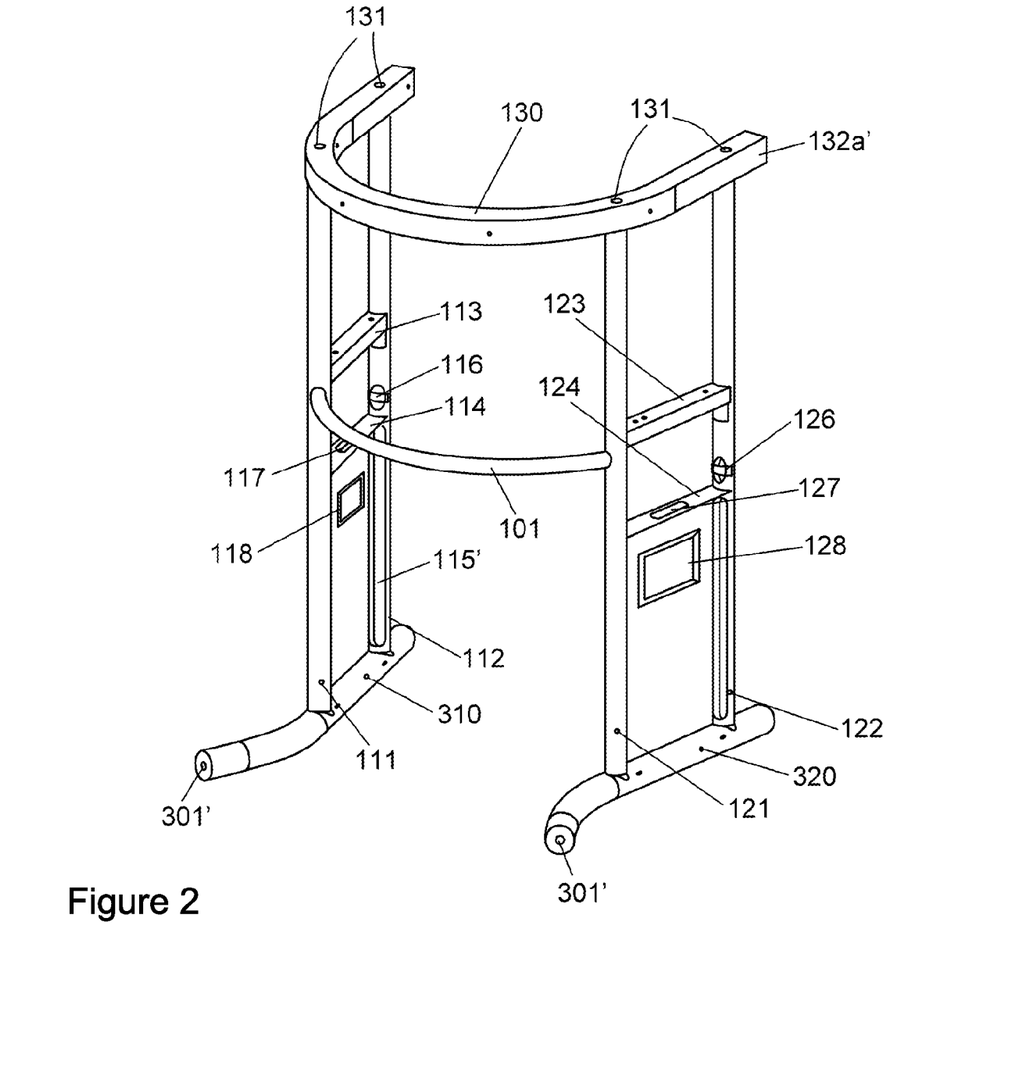
FIG. 2 shows a perspective view of the lower part of a movable radiation protection system without radiation protection drapes according to the first preferred embodiment.

The lower part 100 further comprises a chassis 300 which according to this embodiment has two cantilever arms 310 and 320. Each cantilever arm 310, 320 has the form of a foot that curves outwardly in the direction of escape. Steering rollers 301 are attached to each cantilever arm such that the lower part 100 is seated on the steering rollers. The steering rollers 301 are provided in corresponding housings 301' at the extreme ends of the first cantilever arm 310 and the second cantilever arm 320. The housings 301' for the steering rollers are shown in FIG. 2. The first cantilever arm 310 is attached to the first side part 110 by connecting it to the first tube 111 and the second tube 112 of the first side part 110. Similarly, the second cantilever arm 320 is attached to the second side part 120. The first tubes 111, 121 and the respective second tubes 112, 122 can be connected to the respective cantilever arms 310 and 320 via a screw connection or a welding connection.

The upper ends of the first tubes 111, 121 and the second tubes 112, 122 are connected with a connecting element 130. According to the embodiment, this connecting element 130 has the shape of a semi-circular shaped bracket with a rectangular diameter. The connecting element 130 forms the top end of the first side tubes 111, 121 and the second side tubes 112, 122 in a flush manner. Shank buttons 132a and 132i, respectively, are provided on the outer and inner edges of the connecting element 130 for mounting radiation protection drapes at the outside and/or the inside of the lower frame 100 of the movable radiation protection system. The mounting of the drapes will be explained in more detail below.

In the connecting element 130 are additionally inserted four bearing bushes 131 in corresponding bores. The bores are designed such that they pass through the connecting element so that a passage is provided through the connecting element 130 to the first and second tubes 111, 121, 112, 122.

Second bearing bushes 116, 126 are provided in the first and second tubes 111, 121, 112, 122 at a certain distance from the first bearing bushes 131. According to this embodiment, this distance is in a range of from 30 cm to 40 cm, preferably it amounts to about 35.4 cm.

The upper part 200 comprises four supporting rods 202 which at their respective upper ends are likewise connected with a connecting element 201. The connecting element 201 likewise has a semi-circular bow shape, however with a round cross-section. According to this embodiment, the connecting element 201 is flush with the top of the supporting rods 202.

The bearing bushes 131, 116, 126 of the lower part 100 serve to receive the supporting rods 202 of the upper part 200 so that the supporting rods 202 can be inserted into the bearing bushes and thus into the tubes 111, 121, 112, 122. For this purpose, the bearing bushes 131, 116, 126 of this embodiment have an inner diameter which, with the exception of a certain degree of tolerance, corresponds to the outer diameter of the supporting rods 202. This enables a continuously variable height adjustment of the upper part 200.

The height position of the second part 200 may be additionally fixed by one or more retaining devices 133 which are mounted at the connecting element 130 of the lower part 100. For fixing the height position of the second part 200 by means of the retaining device 133, a screw, e.g. a handscrew, is screwed into a thread which is disposed perpendicular to the longitudinal direction of the bore and extends from an outside of the connecting element up to one of the bores in which the bearing bushes 131 are inserted. The thread extends to the inside of the bore so that the height position of one of the supporting rods 202 of the upper part can be fixed with the end of the inserted screw. According to this embodiment, two such retaining devices 133 are mounted at the respective ends of the connecting element 130.

As already explained, for mounting radiation protection drapes, shank buttons 132a and 132i, respectively, are provided at the lower part 100 both inside and outside of the connecting element 133. If necessary, i.e. depending on the radiation dose to shield, one or more radiation protection drapes may be attached both on the inside and the outside of the lower part 100 of the movable radiation protection system.

At the upper part 200, one or more radiation protection drapes may be placed as cover over the connecting element 201, with part of the one or more radiation protection drapes extending on the front of the movable radiation protection system and the other part extending on the back of the movable radiation protection system. At the side, the one or more radiation protection drapes are closed, for example, with buttons or hook-and-loop fasteners.

FIG. 2 shows a perspective view of the lower part 100 of the movable radiation protection system without radiation protection drapes according to the first preferred embodiment.

At the chassis 300 of the lower part 100, the housings 301' for the corresponding steering rollers 301 are clearly visible on the first cantilever arm 310 and the second cantilever arm 320.

Furthermore, first cross connections 113, 123 and second cross connections 114, 124 are visible at the lower part 100, with which the first tubes 111, 121 and the second tubes 112, 122 of the first side part 110 and the second side part 120, respectively, are connectable for reasons of stability. The second cross connections 114, 124 contain recesses 117, 127. A cable pull or a cable pull system (not shown) passes through these recesses, which connects the upper part 200 with a counterweight or a counter-acting spring 128. Ideally, the counterweight/counter-acting spring 128 is balanced such that it offsets the weight of the upper part 200 and of the radiation protection drape(s) attached to the upper part 200, which is/are attached to the upper part of the frame. Ideally, this compensation ensures that, without further fixation, the upper part 200 and the radiation protection drapes thereon retain their position without further means. Preferably, even with optimal taring, a retaining device 133 or a plurality of retaining devices 133 is provided according to this embodiment. This enables fixation of the upper part 100 at the lower part 200, the overall height being preferably adjustable in steps or continuously.

As shown in FIG. 2, the second bearing bushes 116, 126 are provided in the first tubes 111, 121 and the second tubes 112, 122 at a defined distance from the connecting element 130 of the lower part 100. Moreover, the bores 132a' for the outer shank buttons 132a are visible in the connecting element 130.

Figure 3:
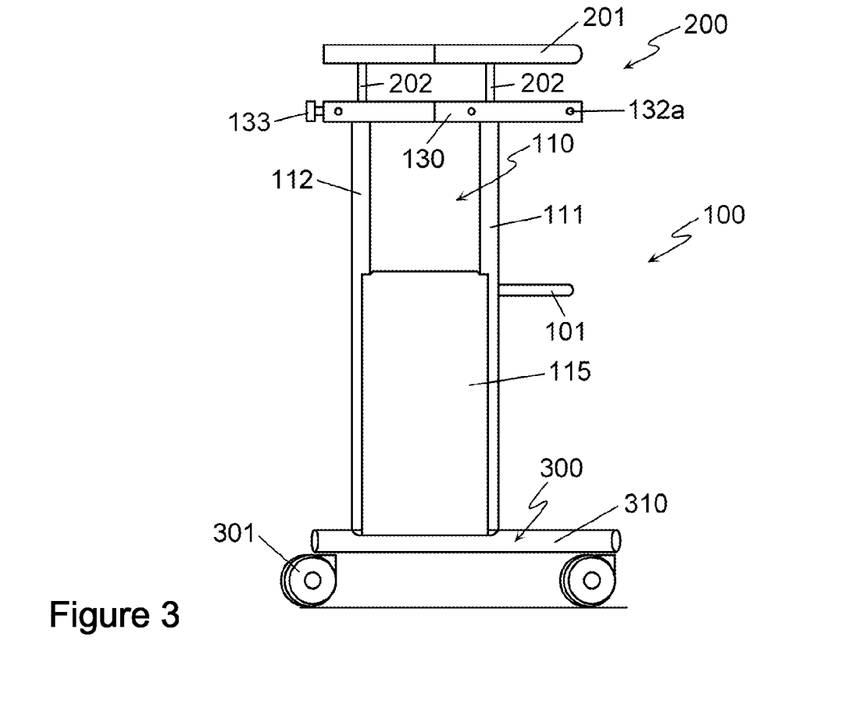
FIG. 3 shows a side view of a movable radiation protection system without radiation protection drapes according to the first preferred embodiment of the present invention.
Figure 4:
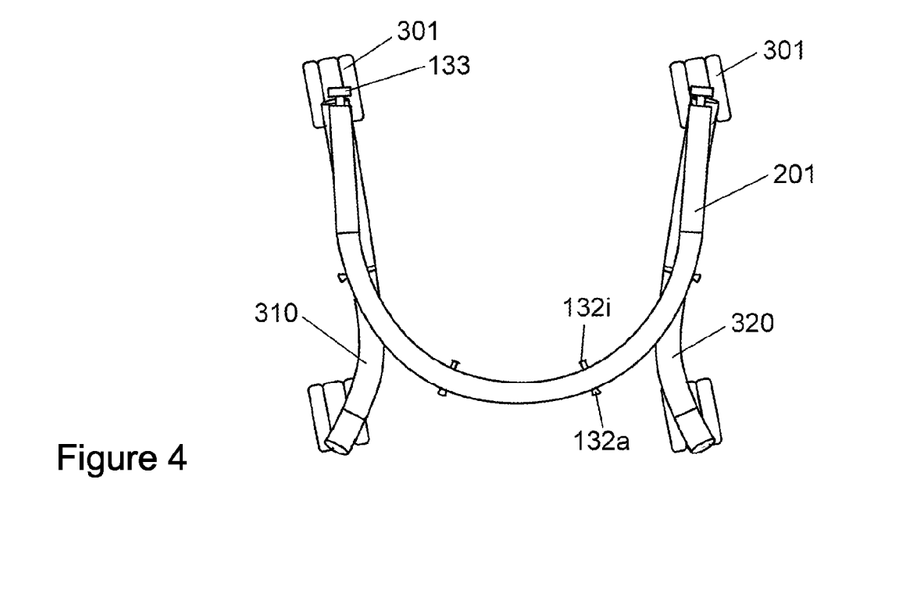
FIG. 4 shows a top view of a movable radiation protection system without radiation protection drapes according to the first embodiment of the present invention.

FIG. 3 shows a side view of the movable radiation protection system without radiation protection drapes according to the first preferred embodiment of the present invention, and FIG. 4 shows a top view of the movable radiation protection system without radiation protection drapes.

Here, FIG. 3 shows the upper part 200 with the connecting element 201 and the supporting rods 202. In addition, FIG.

3 shows the lower element 100 with the chassis 300, as well as the first side part 110 with the first tube 111 and the second tube 112 as well as with the first cover 115. Furthermore, the connecting element 130 is shown with the inner shank buttons 132i and the retaining device 133. FIG. 3 further shows the crossbar 101 which connects the first side part 110 and the second side part 120 with each other.

The top view of FIG. 4 shows in particular the outer shank buttons 132a and the inner shank buttons 132i of the lower part 100, to which one or more radiation protection drapes is/are attachable.

Figure 5:
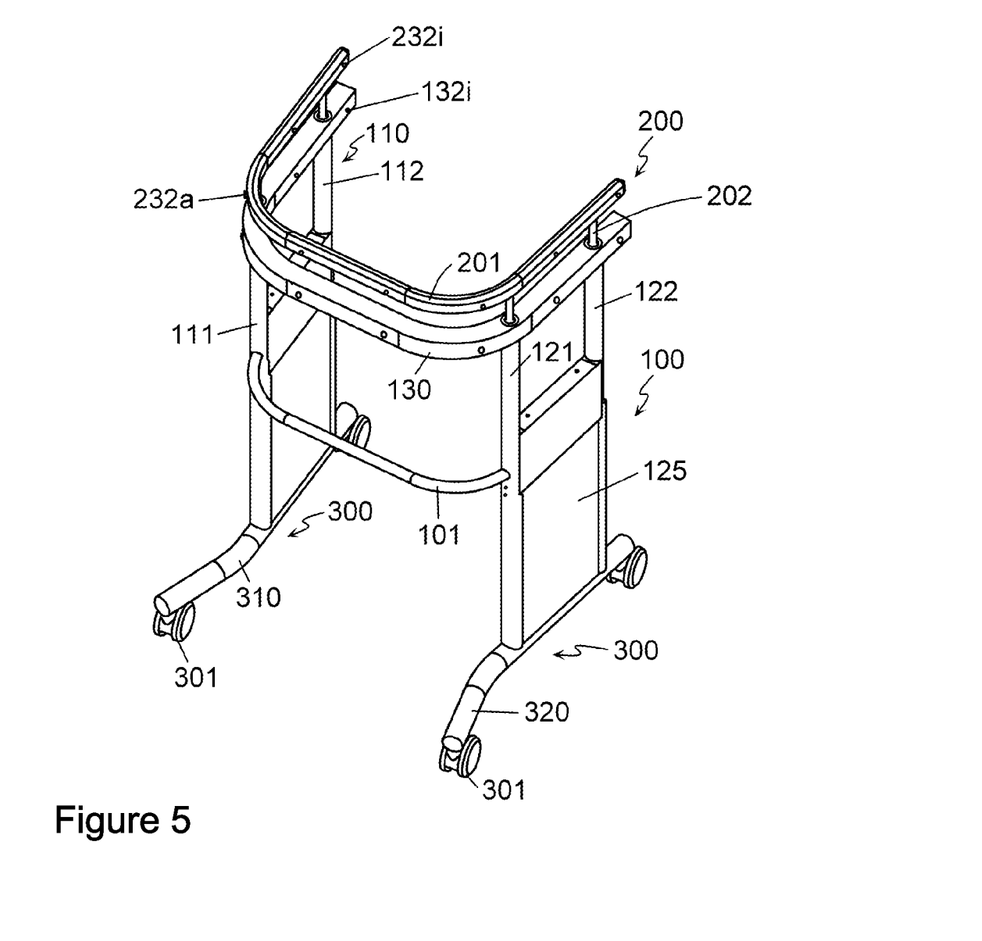
FIG. 5 shows a perspective view of a movable radiation protection system without radiation protection drapes according to a second preferred embodiment of the present invention.

FIG. 5 shows a perspective view of a movable radiation protection system without radiation protection drapes according to a second preferred embodiment of the present invention.

Unlike in the first embodiment, the connecting elements 130 of the lower part 100 as well as 201 of the upper part 200 are not provided in the form of a semi-circular bow, but in the form of a rectangular bow with rounded edges.

A further difference to the first embodiment consists in that the upper part 200 likewise has outer shank buttons 232a and inner shank buttons 232i at the outside and at the inside for mounting one or more radiation protection drapes. Thus, as required, i.e. depending on the dose of radiation, one or more radiation protection drapes can be mounted on the upper part too.

Figure 6A:
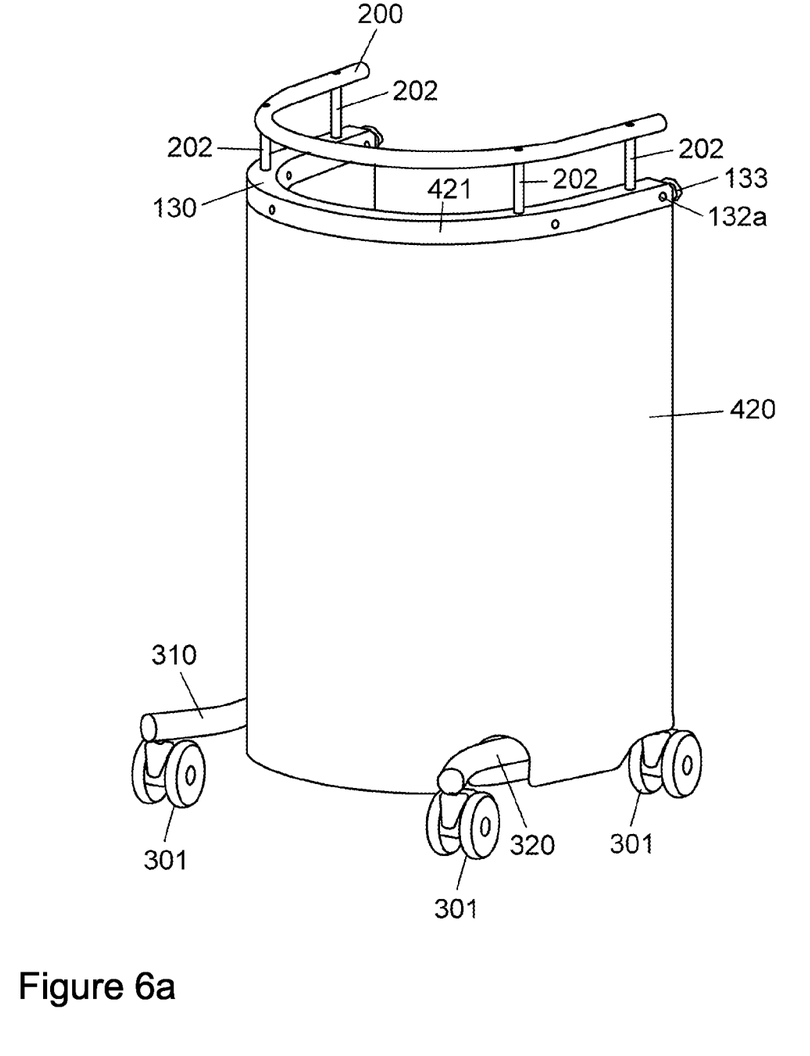
FIG. 6a shows a perspective exterior view of the lower part of a movable radiation protection system with radiation protection drapes according to the first preferred embodiment.

FIG. 6a shows a perspective exterior view of the lower part 100 of a movable radiation protection system with radiation protection drapes according to the first preferred embodiment.

An outer lower radiation protection drape 420 is fastened to the outer shank buttons 132a of the lower part 100 by means of an outer eyelet strip having corresponding eyelets.

Figure 6B:
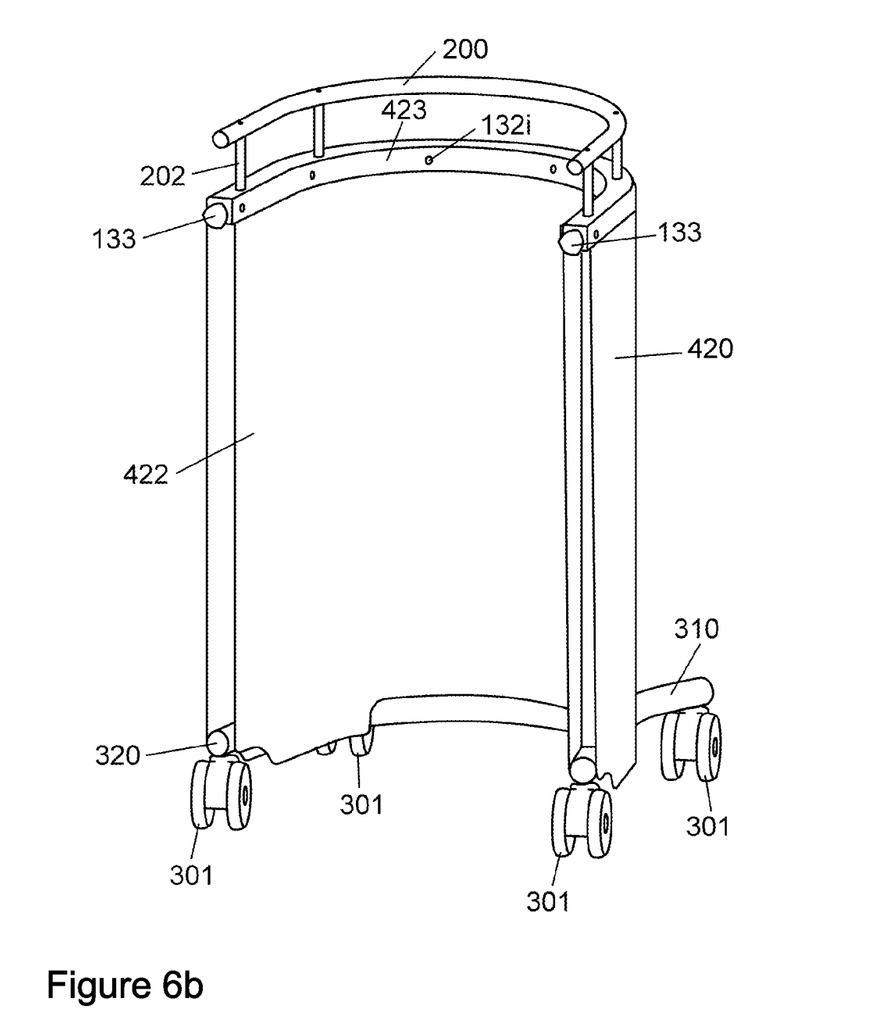
FIG. 6b shows a perspective interior view of the lower part of a movable radiation protection system with radiation protection drapes according to the first preferred embodiment.

FIG. 6b shows a perspective interior view of the lower part 100 of a movable radiation protection system with radiation protection drapes according to the first preferred embodiment.

Here, it can clearly be seen that an inner lower radiation protection drape 422 can be fastened to the inner shank buttons 132i of the lower part 100 by means of an inner eyelet strip 423.

Figure 7A:
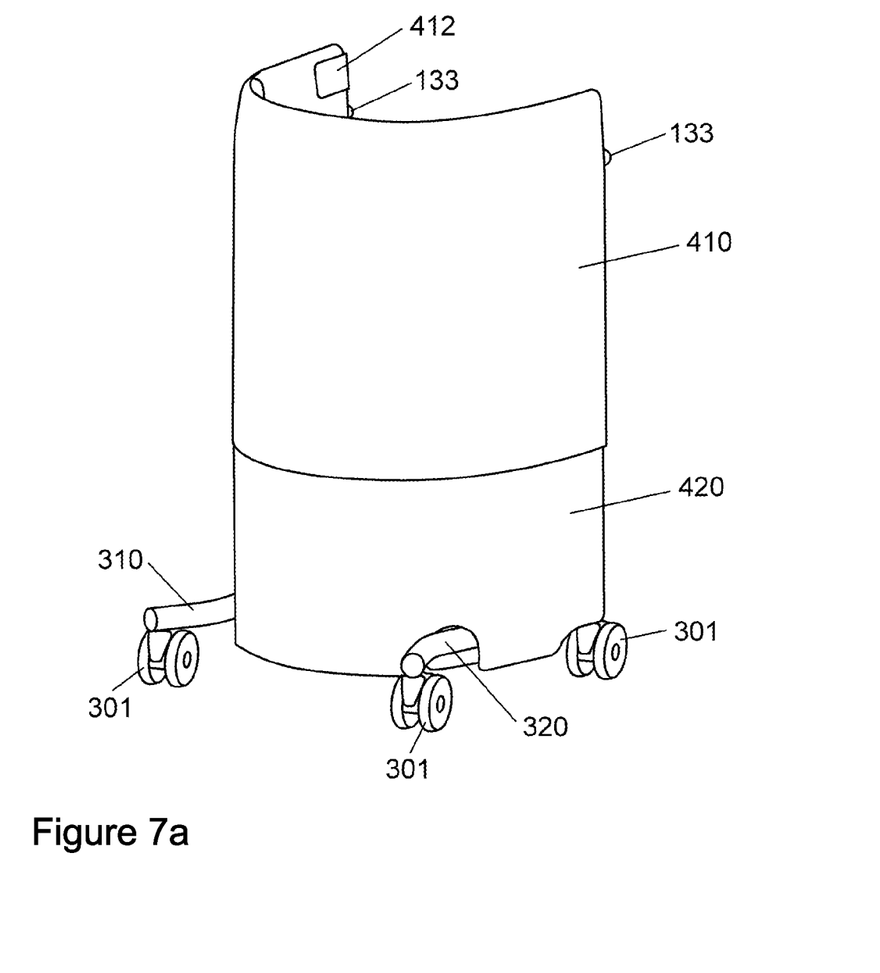
FIG. 7a shows a perspective exterior view of a movable radiation protection system with radiation protection drapes according to the first preferred embodiment.

FIG. 7a shows a perspective exterior view of a movable radiation protection system with radiation protection drapes according to the first preferred embodiment, with the upper part 200 inserted into the lower part 100.

The upper radiation protection drape 410 is formed as cover over the connecting element 201 of the upper part 200 in such a way that both the front and the back of the movable radiation protection system are covered up to a specific point above the chassis 300. According to the first embodiment, the upper radiation protection drape 410 covers the radiation protection system both on the front and on the back up to an area of 40 cm to 55 cm above the chassis, preferably of up to 47 cm above the chassis. On each of the two free upper and free lower ends, a connecting strip 412 is arranged which detachably connects the part of the upper radiation protection drape 410 covering the front of the movable radiation protection system with the part of the upper radiation protection drape 410 covering the back of the movable radiation protection system. According to this embodiment, these connecting strips 412 have a first Velcro strip each with hooks which can be connected to a second Velco strip with loops, the second Velcro strip being arranged on the part covering the back of the movable radiation protection system. This system can also be reversed.

Figure 7B:
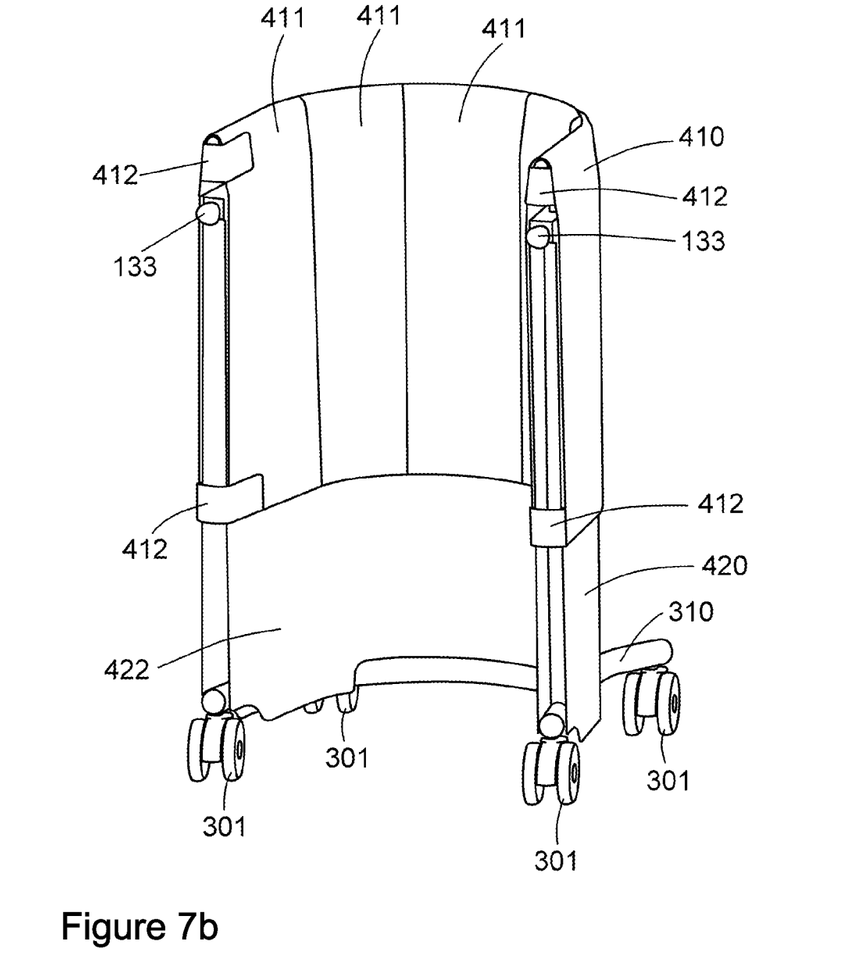
FIG. 7b shows a perspective interior view of a movable radiation protection system with radiation protection drapes according to the first preferred embodiment.

FIG. 7b shows a perspective interior view of a movable radiation protection system with radiation protection drapes according to the first preferred embodiment.

According to this embodiment, the part of the upper radiation protection drape 410 covering the back of the movable radiation protection system is subdivided into individually slotted segments 411. By slitting the parts of the upper radiation protection drape 410 covering the back of the movable radiation protection system into individual segments 411, the upper radiation protection drape 410 can be readily adapted to the curved form of the movable radiation protection system. The segments 411 are dimensioned such that their edges partially overlap so that no radiation can penetrate in the areas of the slits. A total of four connecting strips 412—namely two on each side, i.e. one connecting strip 412 both at the top and the bottom on the one free end and on the opposite free end—are used for connecting the front and the rear parts of the upper radiation protection drape 410.

Although the invention is illustrated and described in detail in the Figures and the respective description, both the illustration and the detailed description should be understood as illustrative and exemplary only, and not as limiting the invention. Of course, persons skilled in the art will be able to make changes and modifications without leaving the scope and the spirit of the following claims. In particular, the invention likewise comprises embodiments with any combination of features that are mentioned or shown above or below with respect to different embodiments.

The present invention also comprises individual features in the Figures even if they are shown therein in combination with other features and/or are not mentioned above or below. Furthermore, the alternatives of embodiments described in the Figures and the description, and individual alternatives and their features may be excluded from the subject-matter of the invention and/or from the disclosed subject-matters. The disclosure covers embodiments exclusively comprising the features described in the claims and/or the exemplary embodiments, and embodiments additionally comprising other features.

The invention claimed is:

1. A movable radiation protection system comprising:
a frame which is open on one side and which comprises a lower part and an upper part, said upper part being vertically adjustable relative to the lower part, at least two flexible radiation protection drapes for protecting against radiation,
wherein a first of the at least two radiation protection drapes is attached to the lower part of the frame and extends preferably to the lower edge of the frame,
wherein a second of the at least two radiation protection drapes is attached to the upper part of the frame and is formed such that the at least two radiation protection drapes overlap in each vertical position in which the upper part is adjusted relative to the lower part,
wherein the first radiation protection drape has an eyelet strip with corresponding eyelets and the lower part has outer shank buttons, and the first radiation protection drape is attached to the outer shank buttons by means of the eyelet strip having the corresponding eyelets, and
wherein a further radiation protection drape has a further eyelet strip with corresponding eyelets and the lower part has inner shank buttons, and the further radiation protection drape is attached to the inner shank buttons by means of the further eyelet strip having the corresponding eyelets.

2. The movable radiation protection system according to claim 1, wherein the lower frame further comprises a chassis.

3. The movable radiation protection system according to claim 2, wherein the chassis comprises a plurality of steering rollers.

4. The movable radiation protection system according to claim 2, wherein the chassis is designed such that a passage is formed over the entire height of the chassis at the side opposite to the open side of the frame.

5. The movable radiation protection system according to claim 3, wherein the chassis comprises a first cantilever arm and a second cantilever arm on which the steering rollers are mounted.

6. The movable radiation protection system according to claim 3, wherein the chassis comprises four steering rollers.

7. The movable radiation protection system according to claim 5, wherein the lower frame comprises a first side part and a second side part.

8. The movable radiation protection system according to claim 5, wherein said first and second cantilever arms are arcuate.

9. The movable radiation protection system according to claim 7, wherein the first cantilever arm is attached to the first side part and the second cantilever arm is attached to the second side part.

10. The movable radiation protection system according to claim 7, wherein the first side part and the second side part comprise first tubes and second tubes in the vertical direction, which are connected with each other by first cross connections and second cross connections.

11. The movable radiation protection system according to claim 10, wherein covers are provided between the first tubes and the second tubes of the first side part and/or the second side part.

12. The movable radiation protection system according to claim 10, wherein the lower part comprises a connecting element which is attached to the first tubes and the second tubes.

13. The movable radiation protection system according to claim 12, wherein said connecting element is bow-shaped.

14. The movable radiation protection system according to claim 7, wherein the first side part and the second side part are connected by a crossbar.

15. The movable radiation protection system according to claim 10, wherein the upper part comprises a plurality of supporting rods and the lower part comprises a plurality of bearing bushes, wherein the supporting rods of the upper part are each movable to and fro in an associated bearing bush for adjusting the height position and wherein the upper part comprises a connecting element.

16. The movable radiation protection system according to claim 15, wherein a part of the bearing bushes is fitted in the connecting element of the lower part and the other part of the bearing bushes is fitted in the first tubes and the second tubes.

17. The movable radiation protection system according to claim 15, wherein the connecting element of the upper part is attached to the supporting rods.

18. The movable radiation protection system according to claim 15, wherein the lower part further comprises a retaining device which is suitable for fixing at least one of the plurality of supporting rods of the upper part so that the upper part is locked in a position in which it is inserted in the lower part.

19. The movable radiation protection system according to claim 1, wherein a counterweight or a counter-acting spring, suitable for compensating for the weight of the upper part and the second radiation protection drape attached to the upper part of the frame, is mounted on the lower part and connected to the upper part.

20. The movable radiation protection system according to claim 1, wherein the radiation protection drapes comprise at least one material containing an element having an atomic number of from 50 to 83.

21. The movable radiation protection system according to claim 1, wherein said at least two flexible radiation protection drapes are for protecting against x-ray radiation.

\* \* \* \* \*